US010987429B2

(12) United States Patent
Shtyrlin et al.

(10) Patent No.: US 10,987,429 B2
(45) Date of Patent: Apr. 27, 2021

(54) INHIBITOR OF ATP-DEPENDENT CELLULAR REVERSE TRANSPORTERS AND METHOD FOR PRODUCING SAME

(71) Applicants: AO "TATKHIMFARMPREPARATY", Kazan (RU); Kazan Federal University, Kazan (RU)

(72) Inventors: Yurij G. Shtyrlin, Kazan (RU); Al'fiya G. Iksanova, Kazan (RU); Yurij V. Badeev, Kazan (RU); Konstantin V. Balakin, Moskovskaya Obl. (RU)

(73) Assignees: AO "Tatkhimfarmpreparaty", Kazan (RU); Kazan Federal University, Kazan (RU)

( * ) Notice: Subject to any disclaimer, the term of this patent is extended or adjusted under 35 U.S.C. 154(b) by 0 days.

(21) Appl. No.: 16/399,472

(22) Filed: Apr. 30, 2019

(65) Prior Publication Data

US 2019/0255184 A1     Aug. 22, 2019

Related U.S. Application Data

(63) Continuation of application No. PCT/RU2017/000809, filed on Oct. 31, 2017.

(30) Foreign Application Priority Data

Nov. 2, 2016  (RU) ................................ 2016143074

(51) Int. Cl.
| | | |
|---|---|---|
| A61K 31/25 | (2006.01) |
| A61K 47/61 | (2017.01) |
| A61K 31/765 | (2006.01) |
| C08G 65/26 | (2006.01) |
| A61K 31/704 | (2006.01) |
| A61K 31/77 | (2006.01) |

(52) U.S. Cl.
CPC .............. *A61K 47/61* (2017.08); *A61K 31/25* (2013.01); *A61K 31/704* (2013.01); *A61K 31/765* (2013.01); *A61K 31/77* (2013.01); *C08G 65/2609* (2013.01); *C08G 65/2696* (2013.01); *C08G 2650/30* (2013.01)

(58) Field of Classification Search
CPC ................................ A61K 47/61; A61K 31/25
See application file for complete search history.

(56) References Cited

FOREIGN PATENT DOCUMENTS

WO      2003/027054 A1    4/2003

OTHER PUBLICATIONS

International Search Report from PCT/RU2017/000809, dated Oct. 31, 2017, dated Feb. 7, 2018.
Abacam General western blot protocol, Guidance for running an efficient and accurate experiment, http://www.abcam.com/ps/pdf/protocols/wb-beginner.pdf.
Choi, Y. H. et al, ABC transporters in multidrug resistance and pharmacokinetics, and strategies for drug development, Curr Pharm. Des., 2014, pp. 793-807, v. 20, No. 5.
Kabanov, A. V. et al., An essential relationship between ATP depletion and chemosensitizing activity of Pluronic block copolymers, J Control Release. 2003, pp. 75-83, v. 91.
Gautherot, J. et al., Effects of Cellular, Chemical, and Pharmacological Chaperones on the Rescue of a Trafficking-defective Mutant of the ATP-binding Cassette Transporter Proteins ABCB1/ABCB4, The Journal of Biological Chemistry, Feb. 10, 2012, pp. 5070-5078, v. 287, No. 7.
Takahashi, K et al., Purification and ATPase Activity of Human ABCA1, The Journal of Biological Chemistry, Apr. 21, 2006, pp. 10760-10768, v. 281, No. 16.
Batrakova, E. V. et al., Effect of pluronic P85 on ATPase Activity of Drug Efflux Transporters, Pharm Res, Dec. 2004, pp. 2226-2233, v. 21, No. 12.
Regev, R. et al., Membrane fluidization by ether, other anesthetics, and certain agents abolishes P-glycoprotein ATPase activity and modulates efflux from multidrug-resistant cells, Eur. J. Biochem., Feb. 1999, pp. 18-24, v. 259.
Tiwari, A.K et al, Revisiting the ABCs of multidrug resistance in cancer chemotherapy, Current Pharmaceutical Biotechnology, 2011, pp. 570-594, v. 12, No. 4.
Batrakova, E.V. et al, Mechanism of sensitization of MDR cancer cells by Pluronic block copolymers: Selective energy depletion, British Journal of Cancer, 2001, pp. 1987-1997, v. 85, No. 12.
Batrakova , E.V. et al, Mechanism of pluronic effect on P-glycoprotein efflux system in blood-brain barrier: contributions of energy depletion and membrane fluidization, J Pharmacol Exp Ther., 2001, pp. 483-493, vol. 299, No. 2.
Chen, Z. et al, Mammalian drug efflux transporters of the ATP binding cassette (ABC) family in multidrug resistance: A review of the past decade, Cancer Letters, 2015 doi: 10.1016/j.canlet.2015.10.010.

(Continued)

*Primary Examiner* — Yong S. Chong
(74) *Attorney, Agent, or Firm* — Patentbar International, P.C.

(57) ABSTRACT

A group of chiral conjugates (optically active hybrid molecules) of oligoetherpolyol structure are inhibitors of ATP-dependent reverse transporters of cells (OEP inhibitors). An OEP inhibitor is a conjugate having an equimolar ratio of optically active polyoxypropylene hexol and polyoxypropylene glycol. The produced preparation increases the efficacy of medicines by inhibiting multi-drug resistance mechanisms of cells. It may be used in biology, pharmacology, pharmaceutics, medicine, and agriculture. The inhibitor is produced by hydroxypropylation of a mixture of sorbitol and a bifunctional oxygen-containing compound in the presence of a hydroxide of an alkaline or alkaline earth metal. The bifunctional oxygen-containing compound used may be water, propylene glycol, dipropylene glycol, tripropylene glycol, tetrapropylene glycol, pentapropylene glycol, hexapropylene glycol, heptapropylene glycol or a mixture thereof. The inhibitor is a conjugate of polyoxypropylene glycol and polyoxypropylene hexol in an equimolar ratio, with a hydroxyl value within a range of 215-240 mg KOH/g.

6 Claims, 9 Drawing Sheets

(56) References Cited

OTHER PUBLICATIONS

Womack, M.D. et al, Detergent effects on enzyme activity and solubilization of lipid bilayer membranes, Biochimica et Biophysica Acta, 1983, pp. 210-215, v. 733.

Iksanova A. G., Olygoester Polyol Based Biologically Active Substances New Delivery System, 01.03.04—Biochemistry, Abstract, Thesis for the degree of Candidate of Biological Sciences, Kazan Federal University, Kazan, 2012.

Solodov, V. A., Polyester Polyols and Water Separation Development Preparations Based Thereon, 02.00.13—petrochemistry, Abstract, Thesis for the degree of Candidate of Technical Sciences, Kazan, 2007.

Cantor, Ch. et al., Biophysical Chemistry, Part II. Techniques for the Study of Biopolymer Structure and Function, 1980, pp. 110-112.

Alakhova D.Y., et al, Effect of doxorubicin/pluronic SP1049C on tumorigenicity, aggressiveness, DNA methylation and stem cell markers in murine leukemia, PLoS One, Aug. 19, 2013; https://www.ncbi.nlm.nih.gov/pubmed/23977261.

SP1049C, Supratek Products, http://www.supratek.com/pipeline/products, Feb. 18, 2013.

Table 2

| | HCT-116 | M-14 | SNB-19 | HCT-15 | A-498 | HSF | MCF-7 | PC-3 | SF-539 | OVCAR-4 | NCI-H322M | CaCo-2 |
|---|---|---|---|---|---|---|---|---|---|---|---|---|
| | Human Colorectal Carcinoma | Human skin melanoma | Human glioblastoma | Human Colorectal Adenocarcinoma | Human Kidney Carcinoma | Conditionally normal human skin fibroblasts | Human Breast Adenocarcinoma | Human Prostate Adenocarcinoma | Human Glyosarcoma | Human Ovarian Adenocarcinoma | Non-small cell human lung carcinoma | Human Colorectal Adenocarcinoma |
| DOX, μM | 0.094 ± 0.004 | 0.188 ± 0.088 | 0.277 ± 0.123 | 0.564 ± 0.381 | 0.799 ± 0.143 | 1.000 ± 0.444 | 1.37 ± 0.313 | 1.44 ± 0.639 | 2.63 ± 0.042 | 2.95 ± 0.72 | 5.39 ± 1.13 | 6.14 ± 0.431 |
| OEP, mg/ml | 1.690 ± 0.330 | 3.104 ± 1.019 | 0.457 ± 0.116 | 5.807 ± 1.095 | 5.827 ± 2.812 | 5.086 ± 0.366 | 1.725 ± 0.856 | 6.067 ± 2.476 | 0.3 ± 0.04 | 4.236 ± 1.238 | 2.169 ± 0.733 | 2.39 ± 1.499 |

Fig. 3

Table 3

| ion m/c | Samples | C OEP [nM] | v OEP [pM] | m in protein [µg] | v OEP / m in protein [pM/µg] |
|---|---|---|---|---|---|
| 442.3368 | OEP 8.7 µg/ml | - | - | 81.8 | - |
| | | 5.93 | 1.19 | 1.50 | 0.7680 |
| | | 31.60 | 6.32 | 22.10 | 0.2860 |
| | OEP 87 µg/ml | 0.34 | 0.07 | 10.80 | 0.0064 |
| | | 7.26 | 1.45 | 27.60 | 0.0526 |
| | | 11.00 | 2.20 | 33.90 | 0.0651 |
| | OEP 870 µg/ml | 4.36 | 0.87 | 14.30 | 0.0609 |
| | | 7.18 | 1.44 | 15.70 | 0.0913 |
| | | 3.29 | 0.66 | 18.10 | 0.0363 |
| 558.4202 | OEP 8.7 µg/ml | 0.33 | 0.07 | 81.90 | 0.0008 |
| | | 9.08 | 1.82 | 1.50 | 1.1800 |
| | | 39.00 | 7.80 | 22.10 | 0.3530 |
| | OEP 87 µg/ml | 1.98 | 0.40 | 10.80 | 0.0367 |
| | | 12.80 | 2.57 | 27.60 | 0.0931 |
| | | 21.80 | 4.35 | 33.90 | 0.1280 |
| | OEP 870 µg/ml | 5.74 | 1.15 | 14.30 | 0.0803 |
| | | 13.80 | 2.75 | 15.70 | 0.1750 |
| | | 7.47 | 1.49 | 18.10 | 0.0827 |
| 616.4619 | OEP 8.7 µg/ml | 0.78 | 0.16 | 81.90 | 0.0019 |
| | | 15.20 | 3.04 | 1.50 | 1.9700 |
| | | 49.50 | 9.89 | 22.10 | 0.4470 |
| | OEP 87 µg/ml | 2.62 | 0.52 | 10.80 | 0.0485 |
| | | 15.60 | 3.11 | 27.60 | 0.1130 |
| | | 24.30 | 4.86 | 33.90 | 0.1430 |
| | OEP 870 µg/ml | 5.65 | 1.13 | 14.30 | 0.0789 |
| | | 16.80 | 3.36 | 15.70 | 0.2130 |
| | | 7.65 | 1.53 | 18.10 | 0.0846 |

INHIBITOR OF ATP-DEPENDENT CELLULAR REVERSE TRANSPORTERS AND METHOD FOR PRODUCING SAME

RELATED APPLICATIONS

This Application is a Continuation application of International Application PCT/RU2017/000809, filed on Oct. 31, 2017, which in turn claims priority to Russian Patent Application RU2016143074, filed Nov. 2, 2016, both of which are incorporated herein by reference in their entirety.

FIELD OF THE INVENTION

The invention refers to the field of development of physiologically active substances, namely, the group of chiral conjugates (optically active hybrid molecules) of oligoetherpolyol nature (OEP), which are inhibitors of ATP-dependent cellular reverse transporters, abbreviated as ABC-transporters (ATP-binding cassette transporters). The invention can be used in the field of biology, pharmacology, pharmaceuticals, medicine, agriculture and ecology to significantly enhance the effectiveness of the action of physiologically active substances, including drugs—anti-tumor, cardiovascular, anti-allergic, anti-inflammatory, and others, by suppressing the mechanisms of multiple drug resistance of cells under the action of the claimed inhibitors of ABC-transporters.

One of the most pressing problems of modern pharmacotherapy is multiple drug resistance of abnormal cells—the innate or acquired immunity of cells to drugs, which differ in their mechanism of action and structure. One of the main mechanisms of the emergence of pathological cells drug resistance is the ability to re-capture and release xenobiotic molecules penetrating into the cell with ATP-dependent pumps of the ABC-transporter family [1].

The ABC-transporter family includes P-gp glycoprotein (P-glycoprotein), multidrug resistance-associated proteins (MRP) and breast cancer resistance proteins (BCRP). The activity of these ABC-transporters, whose expression significantly increases when pathological processes occur in the cell, leads to a significant decrease in the effectiveness of pharmacotherapy. Such effects are shown in detail and studied on the example of most drugs for chemotherapy of tumors [2], including targeted ones, but also in many other pathologies ABC-transporters significantly reduce the effectiveness of drugs. ABC-transporters have a wide substrate specificity, carrying out the reverse capture and release from the cell of many drugs of different therapeutic groups.

As examples, not exhaustive in nature, ABC-transporters substrates are [3]: analgesics (asimadoline, fentanyl, morphine, pentazocine); antibiotics (ampicillin, azithromycin, cefoperazone, ceftriaxone, clarithromycin, doxycycline, erythromycin, gramicidin A, gramicidin D, grepafloxacin, itraconazole, ketoconazole, levofloxacin, rifampicin, sparfloxacin, tetracycline, valinomycin and others); antiviral drugs (delavirdine, lopinavir, lamivudine, nelfinavir, zidovudine); antiarrhythmic drugs (amiodarone, digoxin, lidocaine, propafenone, quinidine, verapamil); anti-cancer drugs (5-fluoruracil, actinomycin D, bisantrin, chlorambuzyl, colchicin, cisplatin, citarabine, daunorubicin, docetaxel, doxorubicin, epirubicin, etoposide, hephytinib, irinotecan, methotrexate, mitomycin C, mitoxantron, paklitaxel, tamoxifen, teniposide, topotecan, vinblastine, vincristine and others); antihistamines (cimetidine, fexofenadine, ranitidine, terfenadine); hypolipidemic drugs (lovastatin, simvastatin, pravastatin, rosuvastatin); calcium channel blockers (azidopine, bepridil, diltiazem, felodipine, nifedipine, nizoldipine, nitrendipine, thiapamil, verapamil); anti-HIV drugs (amprenavir, indinavir, lopinavir, nelfinavir, saquinavir, ritonavir); immunosuppressors (cyclosporine A, sirolimus, tacrolimus), antidepressants (chlorpromazine, phenothiazine) and many other medicinal compounds of natural, synthetic or semi-synthetic origin.

Thus, the creation of effective and safe inhibitors of ATP-dependent cellular reverse transporters is a promising approach to increasing the effectiveness of a wide range of physiologically active substances, including medicines. The creation of such drugs would significantly reduce the therapeutic dose of active substances, and as a consequence, their side effects, and thus make a qualitative leap in pharmacology and medicine.

A wide range of compounds are known from the studied level of technology, including approved drugs that can inhibit ABC-transporters. Thus, a large-scale research work was carried out on the creation of ABC-transporters inhibitors as drugs that increase the sensitivity of cancer cells to the action of anticancer drugs [3]. In particular, as P-gp inhibitors, got active and were studied for combined antitumor chemotherapy atorvastatin, amlodipine, cyclosporine A, disulfiram, nifedipine, verapamil, preparations GF120918, LY475776, LY335979, MS-209, OC144-093, pluronic L61, PSC-833, R101933, S9788, VX-710, XR-9576, V-104. Azithromycin, cyclosporine A, furosemide, glybenclamide, probenecid, MK-571 were studied as inhibitors of MRP2. Cyclosporine A, dipyridamol, elakridar, fumitremorgin C, novobiocin, ortataxel, reserpin, ritonavir, tariquidar, GF120918, VX-710, XR-9576 were studied as BCRP inhibitors.

As it is known from the level of technology, three generations of ABC-transporters inhibitors are distinguished:

Generation 1: cyclosporine A, verapamil (examples). These compounds are effective reverse transport inhibitors, but they themselves have high toxicity. Their use with chemotherapeutic drugs did not lead to significant clinical results.

Generation 2: PSC-833 and VX-710 (examples). These compounds are also effective reverse transport inhibitors. However, their use with chemotherapeutic drugs did not lead to significant clinical results either; in addition, significant side effects of therapy associated with drug-drug interactions were observed.

Generation 3: GF120918, LY335979, R101933 and XR9576 (examples). These compounds are even more effective reverse transport inhibitors on in vitro models than generation 1 and 2 inhibitors. However, their use with chemotherapeutic drugs did not lead to significant clinical results either for reasons of low safety (undesirable side effects) and insufficient therapeutic efficacy.

In general, the current state of research in this field is characterized by local successes at the in vitro level, however, the transition to in vivo, and even more so to clinical studies, as a rule, does not bring the desired effect, mainly due to the presence of undesirable side effects of compositions, non-optimal pharmacokinetics, as well as the lack of effectiveness of the inhibitory effect [3]. At the same time, in all modern researches the prospects of further searches in this direction are noted.

Based on this, it becomes obvious that in order to fully realize the prospects of this approach, more active and safer inhibitors of ABC-transporters are required.

Analogues or prototypes of the claimed technical solution for the matching distinctive features on the date of the application were not identified; however, the applicant identified a large number of means to solve the task for the intended purpose.

The claimed technical solution uses a creative approach which allows at the same time to significantly increase therapeutic efficacy, increase safety, as well as significantly reduce the cost of the active pharmaceutical substance, improve the performance of the production process for obtaining the substance. At the same time, the claimed technical solution provides an opportunity to enter the international market with a product previously unknown in the world.

SUMMARY OF THE INVENTION

The purpose of the claimed technical solution is to obtain an inhibitor of reverse ABC transporters of oligoetherpolyol cells (OEP inhibitor) consisting of polyoxypropylene glycol with a molecular mass of 300 to 500 Da and polyoxypropylene hexol with a molecular mass of 1000 to 1500 Da.

The objectives of the claimed technical solution are achieved by implementing the following chemical process according to the scheme:

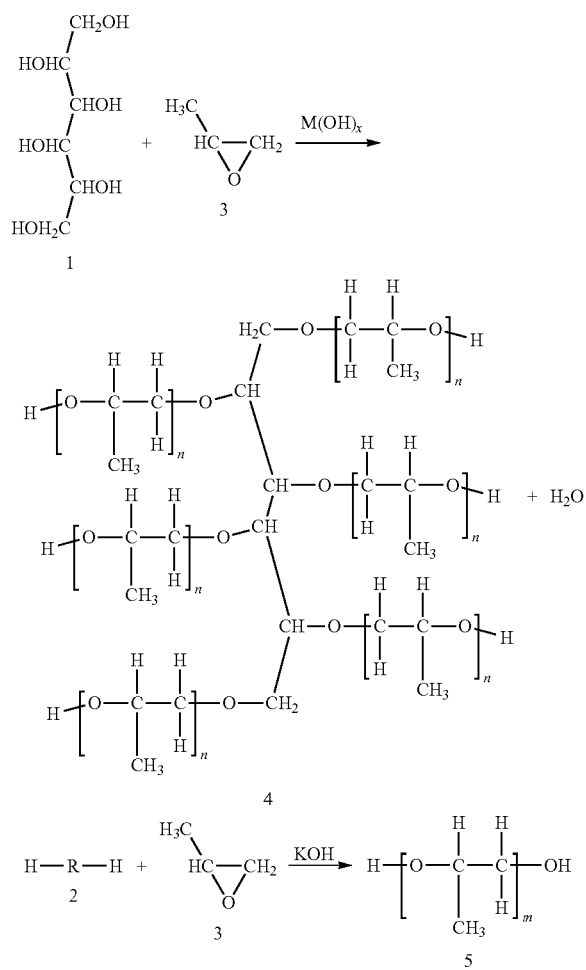

where:
1—sorbitol ((2S,3R,4R,5R)-hexan-1,2,3,4,5,6-hexol);
2—bifunctional oxygen-containing compound in which R=—O—; [—OCH$_2$CH(CH$_3$)]$_k$—O—, k=1-7;

3—propylene oxide;
M(OH)$_x$,—metal hydroxide, where M is alkaline or alkaline earth metal, x=1 or 2;
n=2-6, mostly n=4;
m=5-9, mostly m=7.

Thus, the claimed technical solution for the method is implemented at a time, in one reactor, in one step, using available reagents, taken in proportions providing the desired conjugate with an equimolar ratio of optically active compound 4 and compound 5.

The process as a whole is carried out according to the above scheme, as described below.

The initial reactants 1 and 2 are loaded into the reactor-polymerizer, the alkaline catalyst is added, the stirring is turned on, and the reaction mixture is maintained in nitrogen atmosphere at a temperature of 90-100° C. for 30 minutes to obtain a homogeneous mass. Then, the calculated amount of compound 3 is fed at a rate that provides pressure in the polymerization reactor not higher than 0.39 MPa (4 kgf/cm$^2$), and at a temperature not higher than 115° C. After this, the reaction mass is held at a temperature not higher than 115° C. for 1-1.5 hours until the pressure drop stops.

The ratio of the reactants 1, 2 and M (OH)$_x$ is calculated so that as a result of their reaction with propylene oxide, an equimolar mixture of compounds 4 and 5 is obtained. Compound 4 with n=4 and compound 5 with m=7 are the main oligomeric components formed in the described anionic oligomerization reaction. The amount of compound 3 is calculated so that the equimolar mixture of compounds 4 and 5 obtained has a hydroxyl number in the range of 215-240 mg KOH/g.

Propylene glycol, dipropylene glycol, tripropylene glycol, tetrapropylene glycol, pentapropylene glycol, hexapropylene glycol, heptapropylene glycol, or water, or a mixture of these can act as a bifunctional oxygen-containing compound 2. When an alkali or alkaline earth metal hydroxide interacts with an oxygen-containing compound or sorbitol, water is released, which must also be taken into account when calculating the equimolar ratio of the resulting target products 4 and 5.

For compound 4, the optimal molecular mass is 1200 Da, while it also shows efficacy in the range from 1000 to 1500 Da. For compound 5, the optimal molecular mass is 400 Da, while in the range from 300 to 500 Da it is also effective. Going beyond the specified ranges of molecular masses is also possible, but is accompanied by some decrease in the activity of the resulting inhibitor of ABC-transporters.

An ABC-transporter inhibitor can be obtained by an alternative method, which is not provided by the applicant due to its notability as such, and consists in separately obtaining compounds 4 and 5 by reacting compounds 1 and 2, respectively, with propylene oxide 3 under conditions of alkaline catalysis, with their further mechanical mixing in equimolar amounts.

The invention is illustrated by the following materials:

BRIEF DESCRIPTION OF THE DRAWINGS

FIG. 3. Concentrations of semi-maximum growth inhibition (CC$_{50}$ and IC$_{50}$, µM) of compounds for conditionally normal and tumor human cells.

FIG. 4. The content of the OEP inhibitor in the analyzed cell lysates according to HPLC-MS data.

FIG. 7. Photograph of the results of immunoblotting of the original and genetically modified MCF-7 cells after treatment with doxorubicin, an OEP inhibitor, or their combination for 48 hours.

DETAILED DESCRIPTION OF THE PREFERRED EMBODIMENTS

Figure 1:
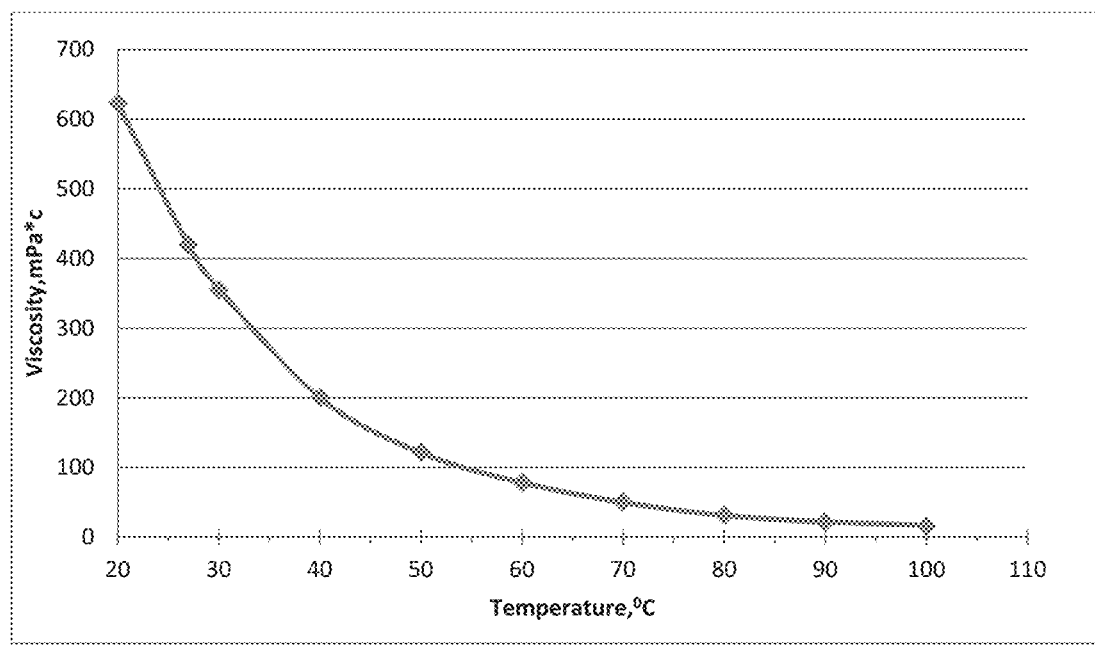
FIG. 1. a plot of the OEP inhibitor viscosity versus temperature.

Further, the applicant presents examples of methods to obtain an OEP inhibitor.

Example 1. Method of Obtaining an OEP Inhibitor from the Sorbitol-Water Starting System 27.3 g (0.15 mol) of sorbitol are loaded into a steel polymerization reactor equipped with a mechanical stirrer, a cooler, a thermocouple, an oxide injection tube, and 0.6 g (0.01 mol) of potassium hydroxide are added to 2.51 g (0.139 mol) of water. The reactor is blown with nitrogen three times. Stirring is activated and it is kept in a nitrogen atmosphere at a temperature of 90-100° C. for 30 minutes to obtain a homogeneous mass. The temperature is raised to 115° C. and 270 g (4.65 mol) of propylene oxide are fed in portions at a rate that provides a pressure in the polymerization reactor not higher than 0.39 mPa (4 kgf/cm$^2$) and the temperature not higher than 115° C. After feeding the calculated amount of propylene oxide, the reaction mass is maintained at a temperature not higher than 120° C. for 1-1.5 hours until the pressure drop stops.

The obtained OEP inhibitor is neutralized with 50% aqueous solution of orthophosphoric acid to a pH of 6.5-7.5, water is removed under vacuum at a temperature of 80-90° C., and filtered with montmorillonite through belting. After all operations, 270 g of slightly yellowish product is obtained. Viscosity is 645 mPa*s, density is 1.038 g/cm$^3$ (20° C.). Hydroxyl number is 220 mg KOH/g (GOST 25261-82 cl. 3.1).

Example 2. Obtaining an OEP Inhibitor from the Starting System of Sorbitol-Propylene Glycol 28.7 g (0.157 mol) of sorbitol are loaded into a steel polymerization reactor equipped with a mechanical stirrer, a cooler, a thermocouple, an oxide injection tube, and 0.63 g (0.01 mol) of potassium hydroxide are added to 10.98 g (0.145 mol) of propylene glycol. The reactor is blown with nitrogen three times. Stirring is activated and it is kept in a nitrogen atmosphere at a temperature of 90-100° C. for 30 minutes to obtain a homogeneous mass. The temperature is raised to 115° C. and 274 g (4.73 mol) of propylene oxide are fed in portions at a rate that provides a pressure in the polymerization reactor not higher than 0.39 mPa (4 kgf/cm$^2$) and the temperature not higher than 115° C. After feeding the calculated amount of propylene oxide, the reaction mass is maintained at a temperature not higher than 120° C. for 1-1.5 hours until the pressure drop stops.

The obtained OEP inhibitor is neutralized with 50% aqueous solution of orthophosphoric acid to a pH of 6.5-7.5, water is removed under vacuum at a bath temperature of 80-90° C., and filtered with montmorillonite through belting. After all operations, 285 g of slightly yellowish product is obtained. Viscosity is 618 mPa*s, density is 1.035 g/cm$^3$ (20° C.). Hydroxyl number is 231 mg KOH/g (GOST 25261-82 cl. 3.1).

Example 3. Obtaining an OEP Inhibitor from the Starting System of Sorbitol-Dipropylene Glycol The reaction was carried out according to the method presented in Example 2. Quantity of starting substances: sorbitol—27.3 g (0.15 mol), KOH—0.6 g (0.011 mol), dipropylene glycol—18.5 g (0.14 mol). The amount of propylene oxide is 255 g (4.4 mol). After neutralization and filtration, 308 g of slightly yellowish product is obtained. Viscosity is 623 mPa*s, density is 1.036 g/cm$^3$ (20° C.). Hydroxyl number is 227 mg KOH/g (GOST 25261-82 cl. 3.1).

Example 4. Obtaining an OEP Inhibitor from the Starting System of Sorbitol-Tripropylene Glycol The reaction was carried out according to the method presented in Example 2. Quantity of starting substances: sorbitol—27.3 g (0.15 mol), KOH—0.61 g (0.011 mol), tripropylene glycol—26.7 g (0.14 mol). The amount of propylene oxide is 246 g (4.24 mol). After neutralization and filtration, 280 g of slightly yellowish product is obtained. Viscosity is 629 mPa*s, density is 1.036 g/cm$^3$ (20° C.). Hydroxyl number is 229 mg KOH/g (GOST 25261-82 cl. 3.1).

Example 5. Obtaining an OEP Inhibitor from the Starting System of Sorbitol-Tetrapropylene Glycol The reaction was carried out according to the method presented in Example 2. Quantity of starting substances: sorbitol—27.29 g (0.15 mol), KOH—0.6 g (0.011 mol), tetrapropylene glycol—34.75 g (0.14 mol). The amount of propylene oxide is 246 g (4.24 mol). After neutralization and filtration, 285 g of slightly yellowish product is obtained. Viscosity is 620 mPa*s, density is 1.034 g/cm$^3$ (20° C.). Hydroxyl number is 233 mg KOH/g (GOST 25261-82 cl. 3.1).

Penta-, hexa-, and heptapropylene glycols were obtained by reacting propylene glycol with propylene oxide under alkaline catalysis conditions. A hydroxyl number was determined for each of the samples.

Example 6. Obtaining an OEP Inhibitor from the Starting System of Sorbitol-Pentapropylene Glycol The reaction was carried out according to the method presented in Example 2. Quantity of starting substances:

sorbitol—27.3 g (0.15 mol), KOH—0.61 g (0.011 mol), pentapropylene glycol—42.8 g (0.14 mol). The amount of propylene oxide is 230 g (3.95 mol). After neutralization and filtration, 285 g of slightly yellowish product is obtained. Viscosity is 627 mPa*s, density is 1.033 g/cm$^3$ (20° C.). Hydroxyl number is 231 mg KOH/g (GOST 25261-82 cl. 3.1).

Example 7. Obtaining an OEP Inhibitor from the Starting System of Sorbitol-Hexapropylene Glycol The reaction was carried out according to the method presented in Example 2. Quantity of starting substances: sorbitol—27.31 g (0.15 mol), KOH—0.6 g (0.011 mol), hexapropylene glycol—50.87 g (0.14 mol). The amount of propylene oxide is 222 g (3.83 mol). After neutralization and filtration, 283 g of slightly yellowish product is obtained. Viscosity is 615 mPa*s, density is 1.037 g/cm$^3$ (20° C.). Hydroxyl number is 225 mg KOH/g (GOST 25261-82 cl. 3.1).

Example 8. Obtaining an OEP Inhibitor from the Starting System of Sorbitol-Heptapropylene Glycol The reaction was carried out according to the method presented in Example 2. Quantity of starting substances: sorbitol—27.3 g (0.15 mol), KOH—0.61 g (0.011 mol), heptapropylene glycol—58.9 g (0.14 mol). The amount of propylene oxide is 214 g (3.83 mol). After neutralization and filtration, 283 g of slightly yellowish product is obtained. Viscosity is 623 mPa*s, density is 1.036 g/cm$^3$ (20° C.). Hydroxyl number is 224 mg KOH/g (GOST 25261-82 cl. 3.1).

The obtained OEP inhibitor is a colorless or slightly yellowish liquid with a viscosity at room temperature of 575-715 MPa*s (FIG. 1 shows the dependence of viscosity of the OEP inhibitor on temperature), with a density in the range of 1.01-1.05 g/cm$^3$ (20° C.). Hydroxyl number is 215-240 mg KOH/g, pH of 10% solution (ethanol/water—70/30) is 5.5-7.5.

Figure 2:
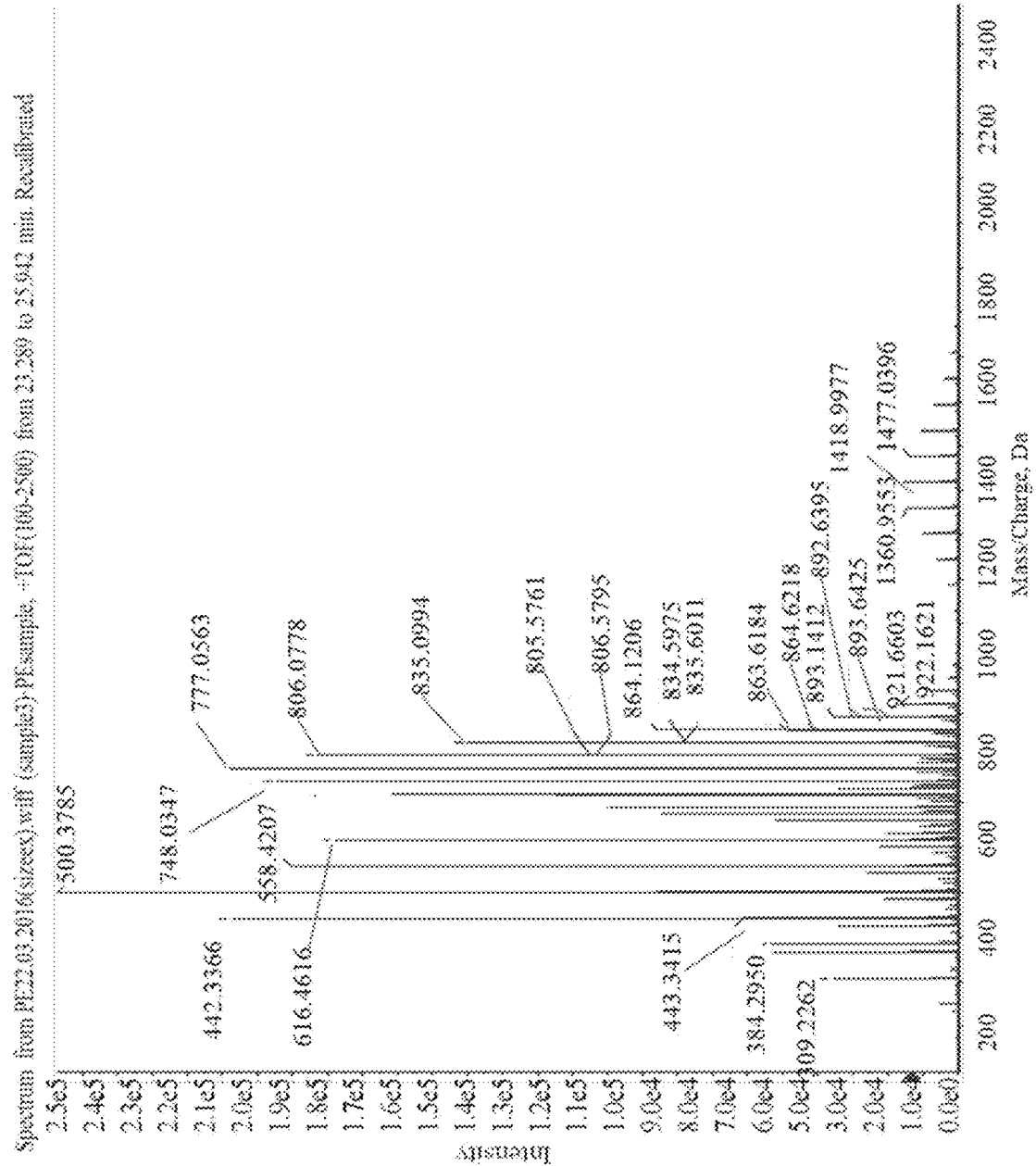
FIG. 2. HPLC-MS spectrum of OEP inhibitor.

An OEP inhibitor is characterized by a set of m/c peaks in the range of both small (400-1200 Da) and heavier masses (1500-2000 Da) (FIG. 2), which reflects the presence of a statistical set of polycondensation reaction products. The analysis was performed using an Agilent ZORBAX Extend-C18 chromatographic column (column size is 1×150 mm, particles size is 3.5 μm) with an Extend Guard pre-column (1×17 mm, particles size is 5 μm) on an Agilent 1260 Binary System chromatograph (vacuum degazifier G1379B, binary gradient pump G1312B, column thermostat G1316A, automatic sampler G1367E, thermostat for automatic sampler G1330 B). The detector is a quadrupol-time-of-flight mass-spectrometer of high resolution AB Sciex 5600 with DuoSpray ionization source. Movable phase: solvent A is a 10 mM solution of ammonium formate in a mixture of water and methanol (90:10%); solvent B is 0.1% formic acid in acetonitrile. The most intense peaks of the OEP inhibitor were used for its quantitative analysis in biological matrices.

The technical result of the claimed technical solution is a method of obtaining chiral conjugates (optically active hybrid molecules) of oligoetherpolyol nature, which are inhibitors of ATP-dependent cellular reverse transporters (OEP inhibitors), to significantly enhance the effectiveness of the action of physiologically active substances from amongst anticancer, cardiovascular, anti-allergic, anti-inflammatory and other medicinal compounds.

Further, the applicant presents the designations and abbreviations that are used to implement the claimed technical solution.

ABC (ATP binding cassette)
APS—ammonium persulfate
ATP (adenosine triphosphate)—adenosine 3-phosphate
C—cytosine
DOX—doxorubicin
EGTA (ethylene glycol-bis(2-aminoethylether)-N,N,N', N'-tetraacetic acid)
FAM—6-carboxyfluorescein
G—guanine
HRP (horseradish peroxidase)
LC—MS—liquid chromatography combined with mass spectrometry
m/c—mass to charge ratio
P-gp—P-glycoprotein
pH—hydrogen index
P$_i$(inorganic phosphate)
T—thymine
U/μL—units in microliter
Vin—vinblastine
$A_{260}$—the value of the wavelength in angstroms at 260 nm
A—adenine
DMSO—dimethylsulfoxide
DNA—deoxyribonucleic acid
DPHT—Diphenylhexatriene
Drugs—medicinal product
DF—dosage form
Mkg—microgram
ML—milliliter
MDR—multiple drug resistance
MTT (3-(4,5-dimethylthiazol-2-yl)-2,5-diphenyltetrazolium bromide, a yellow tetrazole)—tetrazolium dye
RPM—rotations per minute
OEP—oligoetherpolyol
RNA—ribonucleic acid
PSB—phosphate salt buffer
EDTA—ethylenediamintetraacetic acid
Materials and Methods
Chemical Reagents and Materials
Doxorubicin (DOX) hydrochloride, ouabain octahydrate, pentaethylene glycol 98%,
β-mercaptoethanol, ethylene glycol tetraacetic acid (EGTA), beryllium sulfate tetrahydrate, sodium fluoride, ammonium molybdate were purchased from Sigma-Aldrich (USA). Bromphenol blue, sodium deoxycholate, tris-hydrochloride (tris(oxymethyl) amomethane hydrochloride), ammonium persulfate (APS), sodium dodecylsulfate (SDS) are purchased from Amresco (USA). MTT 3-(4,5-Dimethylthiazol-2-yl)-2,5-diphenyltetrazolium bromide) from Life technologies (USA). L-glutamine, Dulbecco's solution, which does not contain Ca$^{2+}$ and Mg$^{2+}$ ions, trypsin-EDTA solution, Hanks solution without phenol red, α-MEM and DMEM media were purchased from PanEco (Russia). 1,6-Diphenyl-1,3,5-hexatriene (DPHT), dithiotreitol (1,4-bis(sulfanyl) butane-2,3-diol), ascorbic acid, cholesterol, Triton® X-100, vinblastine sulfate, ATP disodium salt hydrate, HEPES (4-(2-hydroxyethyl)-1-piperazineethanesulfonic acid) from Acros Organics. Sodium Lauryl Sulfate (SDS) and Ethylenediaminetetraacetic Acid (EDTA) were purchased from Helicon.

Conditions of Cell Cultivation:
Cells MCF-7, MCF-7/Vin, HSF, CaCo-2, HCT-15, HCT-116, OVCAR-4, PC-3, A-498, NCI-H322M, M-14, SNB-19, SF Cells-539 (Table 1) are cultivated in α-MEM medium with the addition of 10% fetal calf serum, L-glutamine and 1% penicillin-streptomycin in an atmosphere of 5% $CO_2$ at 37° C. until a monolayer is formed. To obtain a cell suspension, the monolayer of cells is trypsinized with subsequent inactivation of trypsin by adding α-MEM medium with serum. Cell count is performed in Neubauer chamber by excluding trypan blue. Cells are passaged 2 times a week in the ratio of 1:6.

TABLE 1

List of cell lines used

| Name of cell line | Description | ID NCI-60 (collection of tumor cell lines (US)) |
|---|---|---|
| MCF-7 | Human Breast Adenocarcinoma | ATCC® HTB-22 ™ |
| HSF | Conditionally normal human skin fibroblasts | |
| CaCo-2 | Human Colorectal Adenocarcinoma | ATCC® HTB-37 ™ |
| HCT-15 | Human Colorectal Adenocarcinoma | GSM136289 |
| HCT-116 | Human Colorectal Carcinoma | GSM136288 |
| OVCAR-4 | Human Ovarian Adenocarcinoma | GSM136312 |
| PC-3 | Human Prostate Adenocarcinoma | GSM136316 |
| A-498 | Human Kidney Carcinoma | GSM136294 |
| NCI-H322M | Non-small cell human lung carcinoma | GSM136307 |
| M-14 | Human skin melanoma | GSM136320 |
| SNB-19 | Human glyoblastoma | GSM136283 |
| SF-539 | Human Glyosarcoma | GSM136282 |

Example 9. Exploring Cytotoxic Effect of OEP Inhibitor In Vitro

The effect of the OEP inhibitor on the proliferative potential of human tumor and conditionally normal cells was studied during 72 hours of incubation using the MTT test. 1000 cells were added to the wells of a 96-well plate in 90 µl of culture medium and incubated for 24 hours in a $CO_2$ incubator to make cells adhere to the substrate. Next, aliquots of the prepared solutions of studied compounds (OEP inhibitor) were added in a volume of 10 µl/well. The study was carried out in triplicates. Instead of analyzed compounds, similar volumes of mQ were introduced in the control wells of the plate. After the test substances were applied, the cells were cultured in a $CO_2$ incubator under standard conditions for 72 hours. Next, the culture medium with the test substances was removed from the plate using a vacuum aspirator, the nutrient medium and 5 mg/ml of MTT reagent were added and incubated in a $CO_2$ incubator for 3-4 hours. After the incubation time elapsed, the culture medium with the MTT reagent was removed with a vacuum aspirator, 100 µl of DMSO were added and incubated for 5-10 minutes. Appeared purple staining was detected on a Tecan plate reader at 555 nm (the reference wavelength is 650 nm). The dose-response curves were plotted and the concentration of half maximal cell growth inhibition ($IC_{50}$) was determined. The results are presented in Table 2 in FIG. 3

Thus, a detailed analysis of the table allows us to make unambiguously interpretable conclusions that for the majority of the $IC_{50}$ cells studied, the OEP inhibitor exceeds 1.5 mg/ml, which indicates the complete safety of the claimed conjugate. At the same time, it is possible to ascertain the specificity of the OEP inhibitor for SNB-19 glioblastoma and SF-539 gliosarcoma cells ($IC_{50}$ is 0.46±0.12 mg/ml and 0.46±0.12 mg/ml, respectively), which indicates its some, albeit insignificant own anti-tumor effect on these types of cells.

Example 10. Evaluation of the Effect of the Oep Inhibitor on the Microviscosity of the Plasma Membranes of MCF-7 and MCF-7/Vin Cells A key physico-chemical characteristic of cell membranes that affects their physiological activity is microviscosity, a measure of lipid mobility in the bilayer, which plays an important role in membrane permeability and the functioning of membrane proteins. To assess the plasmalemma microviscosity, a fluorescent method is used, based on the use of a lipophilic indicator of diphenylhexatriene (DPHT), whose fluorescence depends on the cell membrane fluidity.

Cell suspension with a density of $2 \times 10^6$ cells/ml was incubated with DPHT at a final concentration of 1 µM for 30 minutes. Next, aliquots (10 µl) of OEP inhibitor solutions were added to the cell suspension using a multichannel dispenser to a final concentration of 8.7; 87 and 870 µg/ml, as well as doxorubicin at a concentration of 1 µM and its composition with an OEP inhibitor (DOX 1 µM+OEP inhibitor 8.7 µg/ml; DOX 1 µM+OEP inhibitor 87 µg/ml). Cholesterol at a final concentration of 100 µg/ml, as well as the lipophilic detergent Triton X-100 at a concentration of 0.05%, were tested as positive controls that significantly altered the microviscosity of the plasma membranes of cells. Immediately after introducing aliquots of samples, the fluorescence polarization of DPHT was detected for 1 hour with an interval of 10 minutes.

Figure 5:
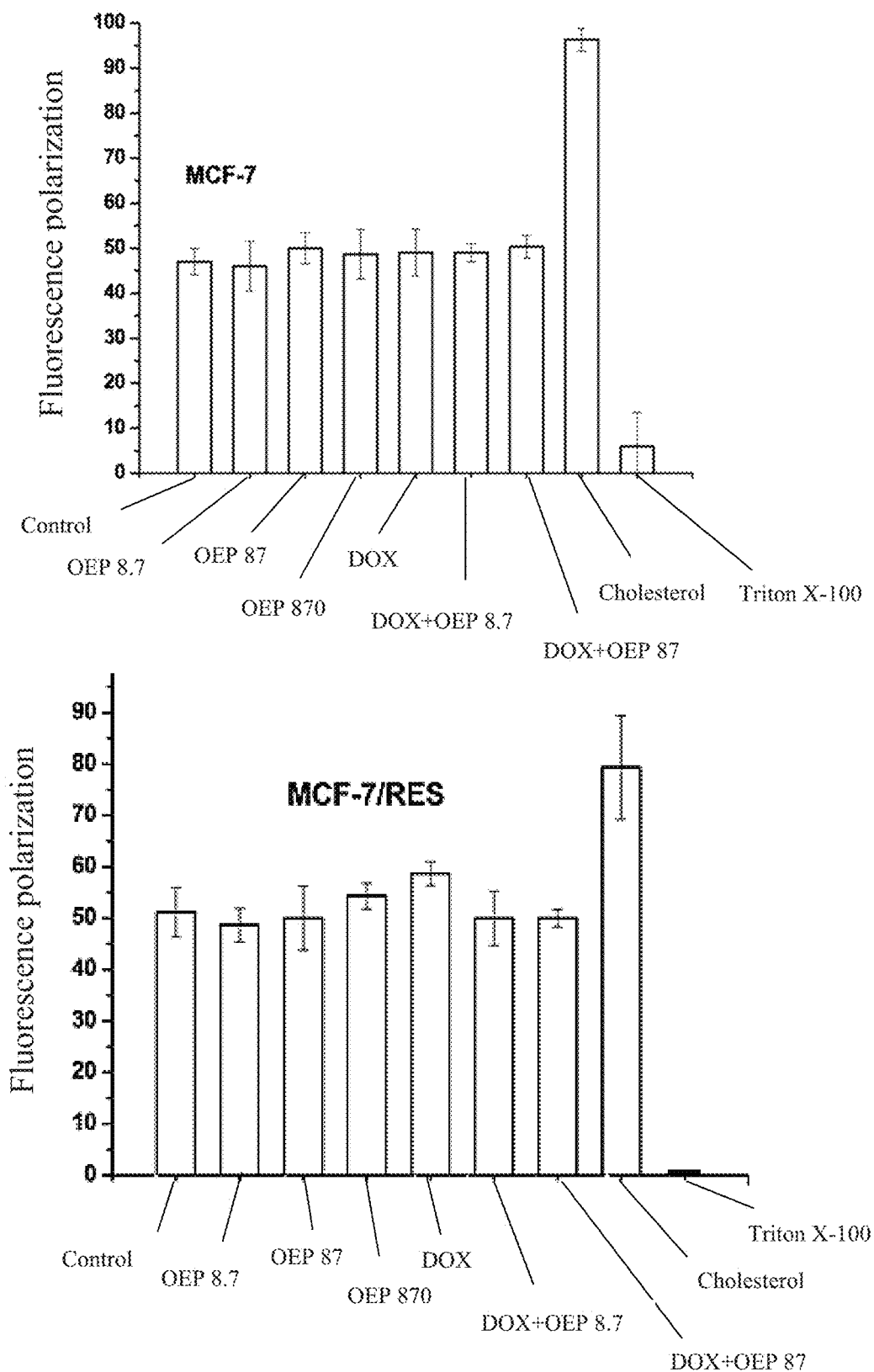
FIG. 5. Polarization of fluorescence of DPHT (1,6-diphenyl-1,3,5-hexatriene) in the cell suspension after adding effectors: OEP inhibitor, composition of doxorubicin and OEP inhibitor, cholesterol and Tritone X-100. (A) MCF-7 cells; (B) cells with MDR MCF-7/Vin. Suspension density is 2×10$^6$ cells/ml, with temperature 25° C., in the following concentrations: OEP inhibitor—8.7, 87 and 870 µg/ml, doxorubicin—1 µM, cholesterol—100 µg/ml, Triton X-100-0.05%.

The results of the effect of the OEP inhibitor on microviscosity of the plasma membranes of MCF-7 and MCF-7/Vin cells are presented in FIG. 5.

Thus, the data obtained indicate that the OEP inhibitor in concentrations of 8.7, 87, and 870 µg/ml, as well as doxorubicin, as well as its compositions with the OEP inhibitor, did not significantly change the polarization of the fluorescence of DPHT in MCF-7 and MCF-7/Vin cell suspensions. Since the polarization of fluorescence is proportional to the viscosity of the fluorophore microenvironment [4], from which it can be concluded that the OEP inhibitor under study did not affect the microviscosity of the plasma membranes of the studied cells. Cholesterol, having a greater viscosity than phospholipids of the plasma membrane, significantly increased the polarization of DPHT fluorescence and microviscosity of the membrane. Triton X-100, being a strong detergent, gradually dissolves the plasma membrane, as evidenced by a significant decrease in the polarization of the DPHT fluorescence. The OEP inhibitor under study had no significant effect on the microviscosity of the cytoplasmic membranes of mammalian cells, which indicates its inertness towards the lipid bilayer of the cytoplasmic membranes of tumor cells.

Example 11. Assessment of the Accumulation of the OEP Inhibitor in Resistant Tumor Cells It is known that some hydrophobic block copolymers of ethylene oxide and propylene oxide have the ability to penetrate the barrier of the plasma membrane of cells, accumulate in the cytoplasm and exert effects on intracellular organelles and enzymes. In particular, it was shown that pluronic P85 has the property to change the microviscosity of mitochondrial membranes and to separate oxidative phosphorylation [5], [6]. In this regard, it was of interest to determine the degree of intracellular accumulation of the tested OEP inhibitor. Identification and quantification of the inhibitor content in cell lysates was performed using liquid chromatography combined with mass spectroscopy (HPLC-MS).

MCF-7/RES cells were dispersed in 6-well plates in an amount of 50,000 cells per well of the plate and cultured at 37° C. and 5% $CO_2$ for 24 hours. Aliquots of the inhibitor were added to the cells, the final concentrations of which were 8.7, 87, and 870 µg/ml and cultured for 96 hours at 37° C. and 5% $CO_2$. Corresponding volumes of deionized water were added to the control samples. After the incubation time elapsed, the medium containing the OEP inhibitor was collected with an aspirator. The cells were separated from the plate surface by suspension with Hanks solution and transferred to 15 ml tubes for washing for at least 5 times (400 g, 4 minutes). 150 µl of deionized water containing an internal standard—pentaethylene glycol with a concentration of $10^{-5}$ M were added to the cell pellet. The cells were lysed by two cycles of freezing and thawing (4 min at −75° C., incubated in a water bath at 37° C. for 2 min) followed by sonication for 4 min. Aliquots of lysates were taken for subsequent determination of the amount of protein in the samples using the Life Technologies Pierce™ BCA Protein Assay Kit. 700 µl of cooled methanol were added to cell lysates, incubated for 15 minutes at −20° C., followed by centrifugation at 17400 g and 0° C. for 20 minutes. The supernatant was transferred to clean tubes and dried under vacuum in a freeze dryer. Immediately prior to analysis, the dried cell lysates were dissolved in 200 µl of 1:1 methanol/water mixture supplemented with 0.1% formic acid. All HPLC-MS experiments were performed using a chromatograph system on an Agilent 1260 Infinity chromatograph (Agilent Technologies, Inc., USA) coupled to an AB Sciex 5600 mass spectrometer (AB Sciex, USA).

The results of the evaluation of the accumulation of the OEP inhibitor in resistant tumor cells are presented in Table 3 in FIG. 4.

HPLC-MS analysis of the intracellular accumulation of the OEP inhibitor showed the presence of femto and picomolar amounts of the polymer in the lysates of the cells that were cultured with the OEP inhibitor (inhibitor concentration: 8.7, 87 and 870 µg/ml, cultivation time is 96 hours). It is noteworthy that with an increase in the concentration of the OEP inhibitor in the culture medium from 8.7 to 870 µg/ml, an increase in the intracellular content is not observed. The absence of concentration dependencies and the low content of the OEP inhibitor in the lysates suggests that the detected traces of the OEP inhibitor are associated with its non-specific adsorption on the plasma membrane and are not due to its penetration into the cytoplasm of the cells. Therefore, it is possible to conclude that the conjugate is highly safe.

Example 12. Evaluation of the Effect of the OEP Inhibitor on the Transepithelial Transport of Doxorubicin Across the Plasma Membrane of CaCo-2 Cells In polarized CaCo-2 cells, the reverse P-gp transporter is located on the apical side of the cytoplasmic membrane and provides reverse transport (B-A) of a large number of substrates, including doxorubicin.

Caco-2 cells were plated into Millicell 96 two-component plates at 10,000 cells/well and incubated for 21 days at 37° C. and 5% $CO_2$. The integrity of the monolayer was checked by measuring the electrical resistance (TEER) using a Millicell-ERS instrument, the experiment was started with a TEER value of at least 3 KΩ/well. To determine the rate of transport of doxorubicin from the apical (A) to the basolateral (B) area [A-B], 90 µl of doxorubicin or doxorubicin and OEP inhibitor (0.087-870 µg/ml) were added to 3 wells with filters and 250 µl of HBSS buffer were added to acceptor wells of the lower plate. To determine the rate of transport from the basolateral (B) to the apical (A) [B-A] area, 90 µl of HBSS buffer were added with 1% DMSO in 3 wells with filters and 250 µl of doxorubicin or doxorubicin and OEP inhibitor (0.087-870 µg/ml) were added in the lower wells of the plate. The assembled Millicell 96 CaCo-2 system was incubated for 2 hours at 37° C. on a shaker with agitation at 300 rpm. Then 70 µl aliquots were taken from each part of the insert and subjected to HPLC-MS analysis using the QTRAP 5500 system (Applied Biosystems) with an Agilent Infinity 1290 chromatograph (Agilent Technologies).

Figure 6:
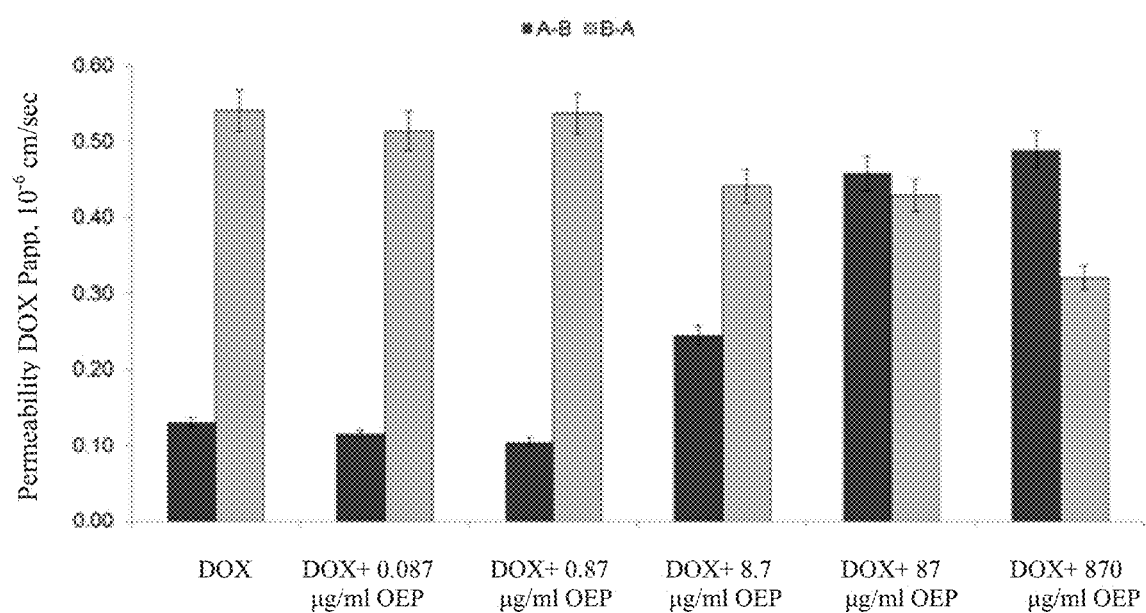
FIG. 6. Histogram of trans-epithelial transport of doxorubicin in polarized CaCo-2 cells. Abbreviations: apical-basolateral transport (A-B), basolateral-apical transport (B-A).

The results of the evaluation of the effect of the OEP inhibitor on the transepithelial transport of doxorubicin are presented in FIG. 6 as the rate of permeability of doxorubicin across the plasma membrane of CaCo-2 cells.

As can be seen, CaCo-2 cells export doxorubicin from the basolateral to the apical part of the membrane (B-A). OEP inhibitor, acting on P-gp located on the apical part of the membrane, inhibits the reverse transport of doxorubicin, increasing its content in the direction A-B: at a concentration of 8.7 µg/ml by 1.9 times, at a concentration of 87 µg/ml by 3.5 times and at a concentration of 870 µg/ml by 3.8 times. Experimental data are presented by the average of three independent experiments±standard deviation. For statistical processing was used Student's criterion for multiple comparisons with the introduction of the Bonferroni correction, P<0.05. Therefore, it seems possible to conclude that the ATP-dependent inhibitor of reverse ABC-transporters is highly effective.

Example 13. Effect of an OEP Inhibitor on the Expression of P-gp (ABCB1)

The OEP inhibitor is able to eliminate the active glycosylated isoform 190 kDa ABCB1, while an inactive high mannose isoform 175 kDa transporter is accumulated in the cells.

MCF-7, MCF-7-ABCC1-DsRed (with over-expression of MRP-1), MCF-7-ABCC2-BFP (with over-expression of MRP-2), MCF-7-ABCB1-GFP (with P-gp over-expression) cells in concentrations of $3\times10^4$ cells/cm$^2$ were cultured in complete DMEM nutrient medium with either doxorubicin added to a final concentration of 3 µM; or an OEP inhibitor to a final concentration of 261 µg/ml; or doxorubicin-OEP inhibitor compositions to a final concentration of 3 µM: 261 µg/ml for 48 hours at 37° C. in the atmosphere of 5% $CO_2$. An adapted and modified ABCAM protocol (http://www.abcam.com/ps/pdf/protocols/wb-beginner.pdf) was used to study proteins by immunoblotting (Western Blot). Monoclonal antibodies to ABCB1 (Cat. No. sc-13131, Santa Cruz) were used at a dilution of 1:200. Anti-mouse antibodies conjugated with HRP—(Cat. No ab6728, Abcam) at a dilution of 1:10,000 were used as secondary. Monoclonal antibodies to β-actin (Cat. No. mAbcam 8226, Abcam) were used at a dilution of 1:2000. The results of the analysis were visualized on ChemiDoc XRS+system (Bio-Rad).

Figure 7:
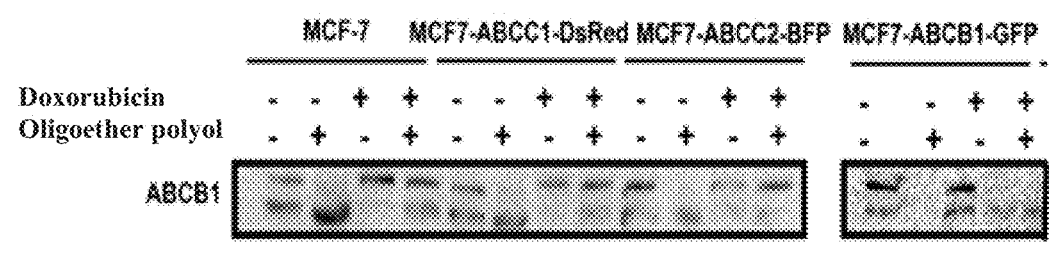

The results of the effect of OEP inhibitor on P-gp expression (ABCB1) are presented in FIG. 7.

ABCB1 protein is represented by 2 isoforms, with a molecular weight of 190 kDa and 175 kDa (FIG. 7, upper and lower bands). At the same time, the 190 kDa isoform is a glycosylated active form of the protein, and the 175 kDa band is a high mannose inactive protein [7]. The results indicate that MCF-7 control cells contain an equivalent amount of active and inactive proteins. Exposure to doxorubicin increases the amount of the active form of the protein, while OEP inhibitor almost completely eliminates the active form of ABCB1. At the same time, an inactive form of the transporter is accumulated in the cells. Cells exposed to the combination drug express both active and high-mannose forms of the protein. Expression of the inactive form proves that the OEP inhibitor was able to partially reverse the doxorubicin-mediated activation of the transporters. We see a similar picture in cells over-expressing the ABCC1 and ABCC2 genes. Therefore, it is possible to conclude that the OEP inhibitor is able to suppress the activity of ATP-dependent inhibitors of reverse ABC-transporters.

Example 14. The Effect of the OEP Inhibitor on the ATP-ase Activity of Membranes with Over-Expression of ABCB1

The ATP-ase activity of the membrane P-glycoprotein was studied using the commercial preparation of isolated insect cell membranes *Spodoptera frugiperda* (Sf9 line) over-expressing human recombinant P-glycoprotein according to the method [8]. ATP hydrolysis during the catalytic activity of P-glycoprotein is accompanied by the formation of inorganic phosphate (Pi), detected by a spectrophotometric reaction. It was shown that the OEP inhibitor inhibits ATP-ase activity with direct concentration dependence—with an increase in concentration, the inhibitory effect increases.

The tested OEP inhibitor at a concentration of 8.7-870 µg/ml was incubated with recombinant membranes over-expressing P-glycoprotein and substrates in 1.5 ml micro-tubes in triplicate. The optical density of the reaction product was measured at 880 nm, proportional to the activity of the reverse transporter and ATP-ase activity of the enzyme. A non-specific enzyme activity inhibitor—beryllium fluoride—was used as controls.

Figure 8:
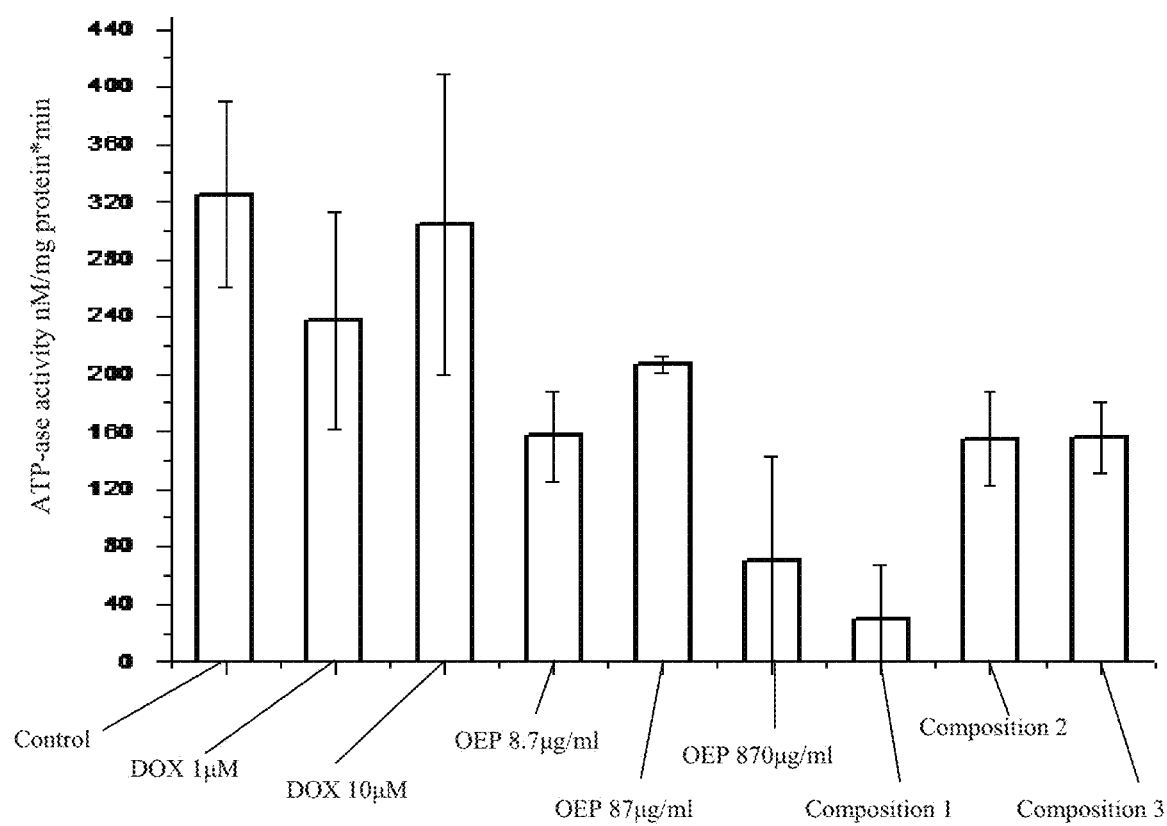
FIG. 8. Effectors action on ATP-ase activity of human P-glycoprotein of isolated membranes of Sf9 cells (0.2 mg/ml by protein). Control: basic activity of membranes in the presence of 5 mmol of ATP and 0.1 mmol of vinblastine.

The obtained values of the ATP-ase activity of human P-glycoprotein of isolated membranes of Sf9 cells in the presence of control inhibitors and tested compounds are presented as a histogram in FIG. 8.

It was established that the OEP inhibitor significantly inhibits the ATP-ase activity of P-glycoprotein. The inhibitory activity of the OEP inhibitor decreases slightly with an increase in its concentration from 8.7 to 87 µg/ml, but it greatly increases at a concentration of 870 µg/ml. In the literature, the prevailing opinion is that amphiphilic block copolymers of ethylene oxide and propylene oxide inhibit the ATP-ase activity of P-glycoprotein due to incorporation into the lipid membrane and changes in the microviscosity of the lipid microenvironment of the transporter [9]-[11]. The OEP inhibitor under study does not significantly change the microviscosity of cell membranes, therefore, its mechanism of action does not exclude the possibility of a direct inhibitory effect on P-glycoprotein. Therefore, it is possible to conclude that the OEP inhibitor significantly suppresses the activity of the ATP-dependent reverse ABC-transporter of P-gp.

Example 15. Effect of the OEP Inhibitor on the Level of ATP in MCF-7, MCF-7/Vin Cells Cell suspension (MCF-7 or MCF-7/Vin) with a density of $2\times10^6$ cells/ml was incubated for 2 hours at 25° C. with an OEP carrier (final concentrations 87, 430 and 2175 µg/ml) or doxorubicin (final concentration 10 µM), or a composition of doxorubicin with an OEP inhibitor at concentrations of 10 µM and 87 µg/ml. Then the cells were precipitated by centrifugation (300 g, 4 minutes) and washed in a buffer solution that activates ATP production in the cells. Buffer composition: NaCl (122 mM), $NaHCO_3$ (25 mM), glucose (10 mM), KCl (3 mM), $MgSO_4$ (1.2 mM), $K_2HPO_4$ (0.4 mM), $CaCl_2$ (1.4 mM) and HEPES (10 mM). The resulting cell pellet was lysed for 5 minutes in chilled lysis buffer with intensive stirring. The composition of the lysis buffer: Tris-HCL (0.05 M), EDTA (2 mM), TritonX100 (1%), NaF (10 mM). Cell lysates were immediately frozen and stored until analysis at −74° C. Immediately prior to analysis, cell lysates were defrosted and centrifuged from cell debris for 7 minutes at 20,000 g, the supernatant was collected for subsequent analysis of ATP content. The content of ATP in cell lysates was determined using the chemiluminescence technique in the reaction involving luciferase, D-luciferin and ATP using the highly sensitive ATP reagent produced by Lumtek. The intensity of chemiluminescence in the luciferin oxidation reaction, proportional to the ATP concentration in the sample, was determined using an Infinite 200 PRO plate reader (TECAN).

Figure 9:
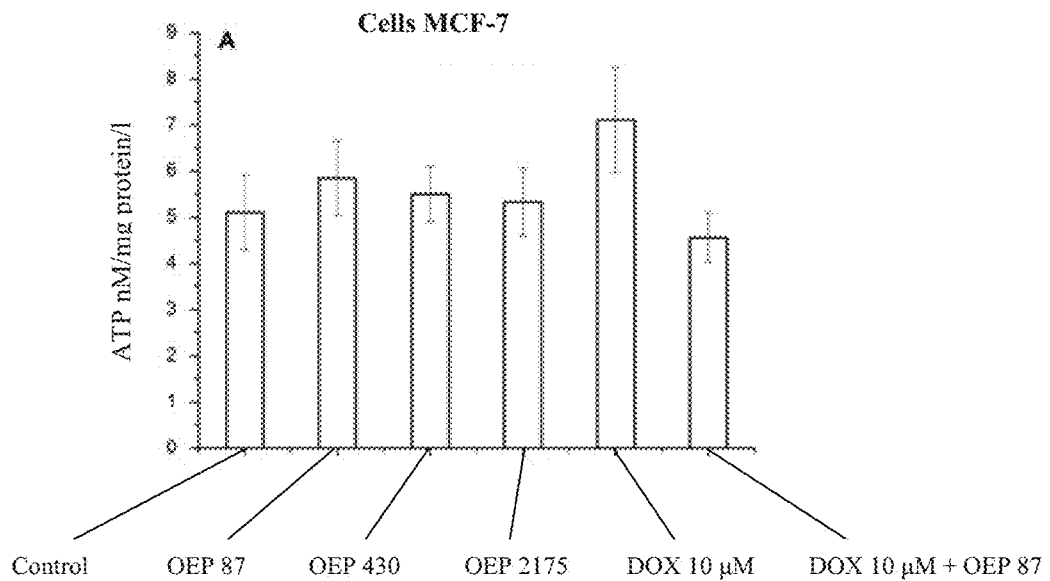
FIGS. 9A-9B. ATP content in the lysates of cells MCF-7 (A) and MCF-7/Vin (B) treated with an OEP-inhibitor (87, 430, 2175 µg/ml), doxorubicin (10 µM) and their composition (OEP inhibitor 87 µg/ml+DOX 10 µM).
Figure 9:
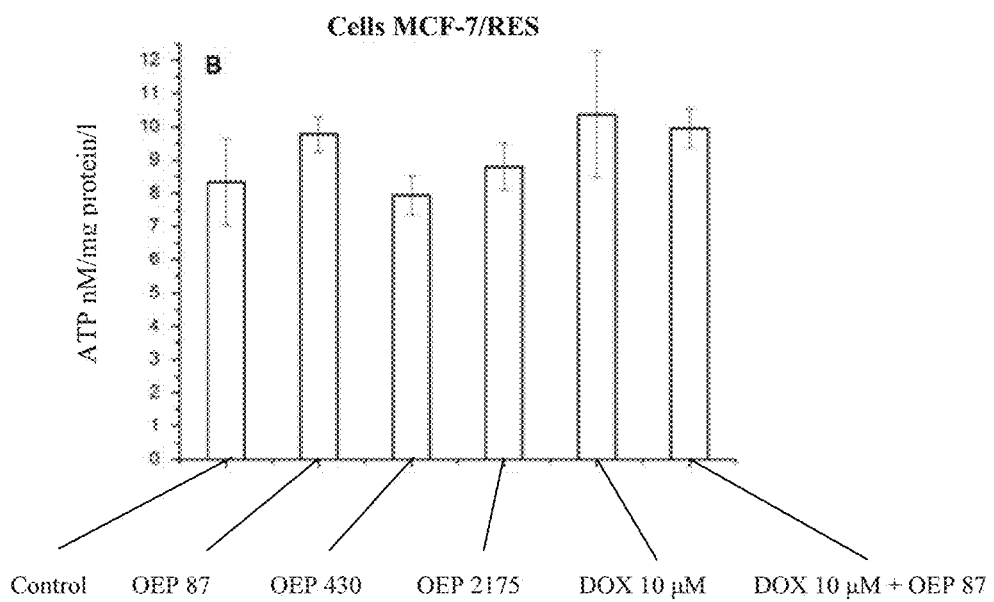

The results of the effect of the OEP inhibitor on the ATP level in MCF-7, MCF-7/Vin cells are presented in FIG. 9.

It has been established that an OEP inhibitor with a 2-hour exposure even at a high concentration does not cause a decrease in the ATP content in MCF-7 and MCF-7/Vin cells. It is known from the literature that hydrophobic block copolymers of ethylene oxide and propylene oxide cause a decrease in ATP content in mammalian cells in culture as a result of penetration into the cytoplasm and impact on the functional state of mitochondrial membranes. In particular, it was shown that pluronic P85 alters the microviscosity of mitochondrial membranes and uncouples oxidative phosphorylation [12], [6]. Comparing the data obtained with the literature data, it can be concluded that the OEP inhibitor under study, due to the nature of the structure, does not penetrate into the cytosol of the cells and does not affect the functions of mitochondria. The combined use of doxorubicin with an OEP inhibitor (OEP inhibitor 87 µg/ml+DOX 10 µM) also did not inhibit ATP biosynthesis in MCF-7 and MCF-7/Vin cells. Therefore, it is possible to conclude that the ATP-dependent inhibitor of reverse ABC-transporters does not affect the ATP biosynthesis process in tumor cells.

Example 16. Parameters of Toxicity of the OEP Inhibitor In Vivo

A study of the acute toxicity of the OEP inhibitor was performed on mice of the CD-1 line (6-8 weeks), Sprague Dawley rats (6-8 weeks) and Soviet Chinchilla rabbits (2-2.5 kg) of both sexes by intravenous and intragastric methods of introduction.

The intragastric administration was carried out to animals deprived of food (for a period of not less than 8 hours) with free access to water. The volume of administration was calculated individually for each animal, based on the body mass recorded immediately before the introduction of the substance. Access to the feed was renewed an hour after the introduction.

The parameters of acute toxicity ($LD_{50}$) of the OEP inhibitor with different routes of administration are shown in Table 4.

TABLE 4

LD$_{50}$ of OEP inhibitor with different routes of administration

| Animal species | Method of administration | Animal sex | OEP inhibitor, mg/kg |
|---|---|---|---|
| CD-1 mice | per os | Males | >5000 |
| | | Females | >5000 |
| | i/a | Males | 1059 |
| | | Females | 1384 |
| SD rats | per os | Males | >5000 |
| | | Females | >5000 |
| | i/a | Males | 1439 |
| | | Females | 1438 |
| Rabbits Soviet chinchilla | per os | Males + females | 4167 |
| | i/a | Males + females | 1183 |

\* per os—intragastric administration
i/a—intravenous administration

According to the obtained results, the OEP inhibitor, when administered intragastrically, according to the degree of toxicity belongs to non-toxic substances, when administered intravenously to low toxic substances. It is known that the most active Pluronic L-61, which is part of the drug SP1049C, which is at the 3rd stage of clinical studies, has a higher toxicity [13]. Thus, the LD$_{50}$ of Pluronic L-61 with an intravenous route of administration in mice corresponds to 800 mg/kg. Therefore, it is possible to conclude that, according to the toxicity class, an ATP-dependent inhibitor of reverse ABC-transporters can be assigned to the class of low-toxic and non-toxic compounds that are safer in comparison with Pluronic L-61.

The above information provided by the applicant leads to the conclusion that the claimed inhibitor of ATP-dependent cellular reverse transporters significantly increases the absorption of drugs by living cells and tissues. At the same time, an inhibitor of ATP-dependent cellular reverse transporters is characterized by high safety and efficacy.

Thus, as a result of experiments, the goal was achieved—a new inhibitor of ATP-dependent cellular reverse transporters was received.

The technical result of the claimed technical solution is that as a result of the research conducted, the OEP inhibitor was obtained by a method that includes preparation of the starting system, oxypropylation of the starting system in the presence of an alkaline catalyst, neutralization of the obtained product, purification to obtain the desired OEP inhibitor, characterized by the fact that the sorbitol ratio: alkaline or alkaline earth metal hydroxide:bifunctional oxygen-containing compound in the starting system is calculated so that as a result of their reaction with propylene oxide, an equimolar mixture of polyoxypropylene glycol and polyoxypropylenehexol is obtained.

The claimed inhibitor of ATP-dependent cellular reverse transporters:
  has a low cytotoxicity against human cell cultures compared with most of the inhibitors of ABC-transporters described in the literature;
  does not affect the microviscosity of cytoplasmic membranes of tumor cells of the MCF-7 line and MCF-7/RES cells with acquired drug resistance;
  does not penetrate the cytoplasmic membrane into the tumor cells of MCF-7;
  in the concentration range of 8.7-870 μg/ml, it causes specific inhibition of P-gp-mediated reverse transport of doxorubicin, increasing its concentration in acceptor wells by 1.9-3.8 times, respectively;
  is able to eliminate the active glycosylated isoform 190 kDa ABCB1, while an inactive high mannose isoform 175 kDa of transporter is accumulated in the cells.
  inhibits the ATP-ase activity of isolated membranes of Sf9 cells with over-expression of human P-glycoprotein;
  does not change the intracellular level of ATP;
  when administered intragastrically, according to the degree of toxicity belongs to non-toxic substances, when administered intravenously—to low toxic substances;
  characterized by ease of production, cheap raw materials, production can be carried out at existing enterprises of the chemical industry.
  provides the opportunity to enter the international market with a product previously unknown in the world.

The list of references includes some publications describing the state of the art to which the claimed technical solution relates.

At the same time, it should be noted that, based on the claimed technical solution, it is possible to carry out various kinds of modifications and/or changes without going beyond the scope of patent claims.

The claimed technical solution meets the criterion of "novelty" applied to the inventions on the set of features given in the independent claim of the invention, since this set of features was not identified from the level of technology studied by the applicant.

The claimed technical solution meets the criterion of "inventive step" applied to inventions because the obtained inhibitor of ATP-dependent cellular reverse transporters and the method to obtain it provide the possibility of solving previously unsolvable problems, namely, with a significant increase in therapeutic efficacy, to significantly increase safety, and also significantly reduce the cost of the finished dosage form.

The claimed technical solution meets the criterion of "industrial applicability" applied to the inventions as it can be used in production at specialized enterprises, using known materials, equipment and technology.

LIST OF REFERENCES USED

1 Choi Y. H., ABC transporters in multidrug resistance and pharmacokinetics, and strategies for drug development/Y. H. Choi, A. M. Yu//Curr. Pharm. Des. 20 (2014), P. 793-807
2. Tiwari A. K. Revisiting the ABCs of multidrug resistance in cancer chemotherapy/A. K. Tiwari, K. Sodani, C. L. Dai, C. R. Ashby Jr., Z. S. Chen//Curr. Pharm. Biotechnol. 12 (2011), P. 570-594
3. Chen Z., Mammalian drug efflux transporters of the ATP binding cassette (ABC) family in multidrug resistance: A review of the past decade./Z. Chen, T. Shi, L. Zhang, P. Zhu, M. Deng, C. Huang, T. Hu et al.//Cancer Letters, 370 (2016), P. 153-164
4. C. Kantor Biophisicheskaya chimiya [Biophysical chemistry]. Volume 2. Metody issledovania struktury i funktsii biopolimerov/[Methods of study of structure and function of biopolymers] C. Kantor, P. Shimmel,—Moscow: MIR Publ., 1985.
5. Batrakova E. V. Mechanism of sensitization of MDR cancer cells by Pluronic block copolymers: Selective energy depletion/E. V. Batrakova, S. Li, W. F. Elmquist et al.//Br J Cancer.—2001.—V. 85, N. 12.—P. 1987-1997.
6. Kabanov A. V. An essential relationship between ATP depletion and chemosensitizing activity of Pluronic block copolymers/A. V. Kabanov, E. V. Batrakova, V. Y. Alakhov//J Control Release. 2003.—V. 91, N. 1-2.—P. 7583.
7. Gautherot, J. Effects of Cellular, Chemical, and Pharmacological Chaperones on the Rescue of a Trafficking-defective Mutant of the ATP-binding Cassette Transporter Proteins ABCB1/ABCB4/J. Gautherot, A-M. Durand-Schneider, D. Delautier, J-L. Delaunay, A. Rada, J. Gabillet, C. Housset, M. Maurice, T. Aït-Slimane//HEJOURNAL OF BIOLOGICAL CHEMISTRY.—2012.—Vol. 287.—No. 7.—P.5070-5078.
8. Takahashi, K. Purification and ATPase Activity of Human ABCA1/K. Takahashi, Y. Kimura, N. Kioka, M. Matsuo, K. Ueda//The Journal of biological chemistry. 2006. Vol. 281, no. 16. P. 10760-10768.
9. Batrakova, E. V. Effect of pluronic P85 on ATPase activity of drug efflux transporters/E. V. Batrakova, S. Li, Y. Li, V. Y. Alakhov, A. V. Kabanov//Pharm Res. 2004. V. 21, N. 12. P. 2226-2233.
10. Regev, R Membrane fluidization by ether, other anesthetics, and certain agents abolishes P-glycoprotein ATPase activity and modulates efflux from multidrug-resistant cells/R. Regev, Y. G. Assaraf, G. D. Eytan//Eur J Biochem. 1999. Vol. 259. pp. 18-24.
11. Womack, M. D. Detergent effects on enzyme activity and solubilization of lipid bilayer membranes/M. D. Womack, D. A. Kendall, R. C. MacDonald//Biochimica et Biophysica Acta (BBA)—Biomembranes.—1983.—Vol. 733.—No 2.—P. 210-215.
12. Batrakova, E. V. Mechanism of pluronic effect on P-glycoprotein efflux system in blood-brain barrier: contributions of energy depletion and membrane fluidization/ E. V. Batrakova, S. Li, S. V. Vinogradov et al.//J Pharmacol Exp Ther.—2001.—Vol. 299.—No. 2.—P. 483-493.
13. SP1049C [Electronic resource].—2016.—Mode of access: http://www.supratek.com/pipeline/products

What is claimed is:

1. An inhibitor of ATP-dependent cellular reverse transporters of a group of chiral conjugates, the chiral conjugates being oligoetherpolyolic optically active hybrid molecules, the inhibitor being a mixture of polyoxypropylenehexol of formula

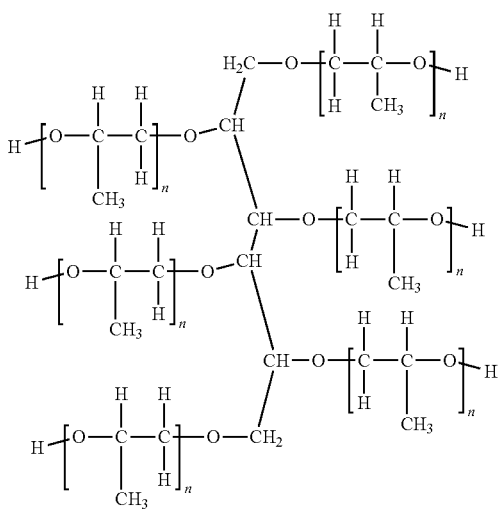

and a polyoxypropylene glycol of formula

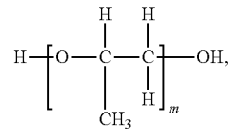

wherein n is from a range of 2 to 6 and wherein m is from a range of 5 to 9.

2. The inhibitor of claim 1, wherein the molecular mass of the polyoxypropylenehexol is 1200 Da, and wherein the molecular mass of the polyoxypropylene glycol is 400 Da.

3. The inhibitor of claim 1 wherein the molar ratio of the polyoxypropylenehexol and the polyoxypropylene glycol is 1:1.

4. The inhibitor of claim 1, wherein n is 4 and wherein m is 7.

5. The inhibitor of claim 4, wherein the molecular mass of the polyoxypropylenehexol is 1200 Da, and wherein the molecular mass of the polyoxypropylene glycol is 400 Da.

6. The inhibitor of claim 4, wherein the molar ratio of the polyoxypropylenehexol and the polyoxypropylene glycol is 1:1.

* * * * *

UNITED STATES PATENT AND TRADEMARK OFFICE
CERTIFICATE OF CORRECTION

PATENT NO. : 10,987,429 B2  
APPLICATION NO. : 16/399472  
DATED : April 27, 2021  
INVENTOR(S) : Yurij G. Shtyrlin et al.

Page 1 of 1

It is certified that error appears in the above-identified patent and that said Letters Patent is hereby corrected as shown below:

On the Title Page

Item (72) Inventors should read: Yurij G. SHTYRLIN, Kazan (RU); Al'fiya G. IKSANOVA, Kazan (RU); Yurij V. BADEEV, Kazan (RU); Konstantin V. BALAKIN, Shchelkovo (RU)

Signed and Sealed this  
Twenty-fourth Day of August, 2021

Drew Hirshfeld  
*Performing the Functions and Duties of the*  
*Under Secretary of Commerce for Intellectual Property and*  
*Director of the United States Patent and Trademark Office*